(12) United States Patent
Kuramoto et al.

(10) Patent No.: US 11,266,130 B2
(45) Date of Patent: Mar. 8, 2022

(54) DEVICE AND METHOD FOR TESTING INSECT REPELLENCY

(71) Applicant: Kaken Test Center, Tokyo (JP)

(72) Inventors: Kanya Kuramoto, Tokyo (JP); Hitoshi Kawada, Nagasaki (JP)

(73) Assignee: KAKEN TEST CENTER, Tokyo (JP)

( * ) Notice: Subject to any disclaimer, the term of this patent is extended or adjusted under 35 U.S.C. 154(b) by 454 days.

(21) Appl. No.: 16/468,056

(22) PCT Filed: Dec. 27, 2016

(86) PCT No.: PCT/JP2016/088873
§ 371 (c)(1),
(2) Date: Jun. 10, 2019

(87) PCT Pub. No.: WO2018/122952
PCT Pub. Date: Jul. 5, 2018

(65) Prior Publication Data
US 2020/0053993 A1   Feb. 20, 2020

(51) Int. Cl.
*A01K 67/033* (2006.01)
*A01M 29/12* (2011.01)
(Continued)

(52) U.S. Cl.
CPC ............ *A01K 67/033* (2013.01); *A01K 1/031* (2013.01); *A01M 29/12* (2013.01);
(Continued)

(58) Field of Classification Search
CPC .................... A01M 2200/01; A01K 2227/706
See application file for complete search history.

(56) References Cited

U.S. PATENT DOCUMENTS

| 5,074,247 A | 12/1991 | Gupta et al. |
| 2006/0260548 A1 | 11/2006 | Palomino et al. |

FOREIGN PATENT DOCUMENTS

| CN | 203000126 U | 6/2013 |
| CN | 203040392 U | 7/2013 |

(Continued)

OTHER PUBLICATIONS

First Examination Opinion Notice for Chinese Patent Application No. 201680091513.5 and the English machine translation, State Intellectual Property Office of China, dated Dec. 23, 2020.
(Continued)

*Primary Examiner* — Maurice C Smith
(74) *Attorney, Agent, or Firm* — Florek & Endres PLLC

(57) ABSTRACT

In a housing (1), an internal space capable of housing an insect is formed, an opening (11) through which the internal space and an outside communicate with each other is formed, and a portion other than the opening (11) is closed so that the insect is incapable of passing through the portion. Rails (2) in a pair are disposed in parallel with each other on both sides of the opening (11) across the opening (11) on an outer surface of the housing (1), maintain a gap between a face, on which the opening (11) is formed, of the housing (1) and a cover (3) to have a size preventing the insect from passing through the gap, and slidably retain the cover (3) on the external side of the housing (1). A sample holder retains a sample, is slidably retained by the rails (2), and enables the sample to be exposed from the opening (11) to the internal space when being slidably retained by the rails (2) in the state of retaining the sample. The cover (3) and the sample holder retaining the sample can be slid between the rails (2) in the pair in a state in which one side of the cover (3) and one side of the sample holder come into contact with each other, whereby the cover (3) and the sample holder can be moved between a position at which the cover (3) covers the
(Continued)

opening (11) and a position at which the sample covers the opening (11).

9 Claims, 9 Drawing Sheets

(51) Int. Cl.
*A01K 1/03* (2006.01)
*G01N 33/00* (2006.01)

(52) U.S. Cl.
CPC .... *A01K 2227/706* (2013.01); *A01K 2267/00* (2013.01); *A01M 2200/01* (2013.01); *G01N 33/00* (2013.01)

(56) References Cited

FOREIGN PATENT DOCUMENTS

| | | |
|---|---|---|
| CN | 203340767 U | 12/2013 |
| JP | 2004290144 A | 10/2004 |
| JP | 2005023439 A | 1/2005 |
| JP | 2006169209 A | 6/2006 |
| JP | 2006322719 A | 11/2006 |
| JP | 2010126486 A | 6/2010 |
| JP | 2013136524 A | 7/2013 |
| JP | 2015172006 A | 10/2015 |
| WO | 2009025131 A1 | 2/2009 |

OTHER PUBLICATIONS

Sommer, Jean, "Extended European Search Report (EESR) for EP Patent Application No. 16925953.8," European Patent Office, dated Jun. 9, 2020.

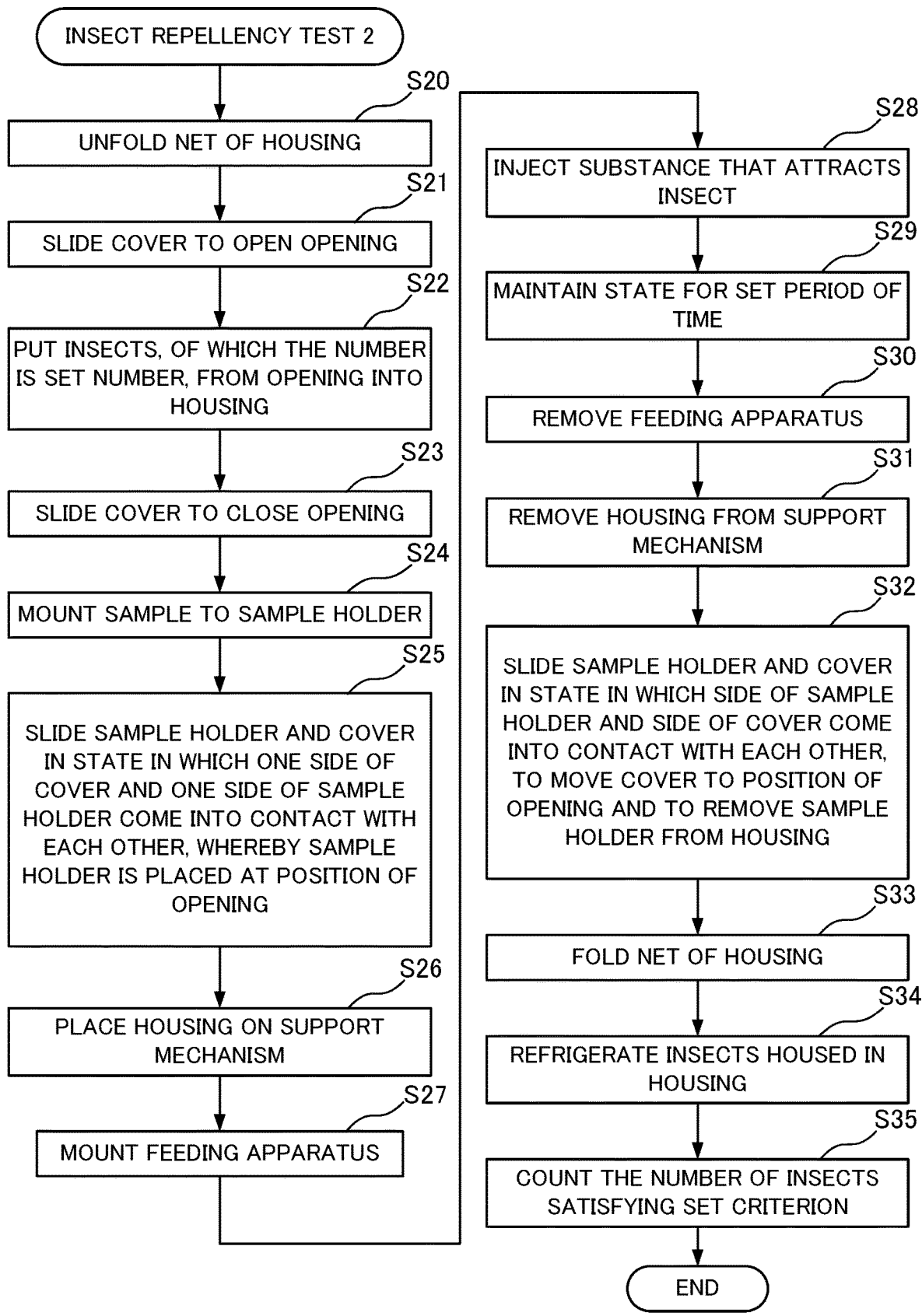

DEVICE AND METHOD FOR TESTING INSECT REPELLENCY

TECHNICAL FIELD

The present disclosure relates to an apparatus for testing insect repellency and a method for testing insect repellency.

BACKGROUND ART

Insecticides, repellents, and insect repellent agents have been proposed and put to practical use in order to repel unpleasant or harmful insects in the life of humans or pets. Objective testing of insect repellent performance is required for investigating the effects of such insecticides, repellents, or insect repellent agents.

For example, paragraph [0021] of Patent Literature 1 describes that one arm of an experimenter, on which a sack-shaped test cloth is slipped, is inserted into a fabric cage in which mosquitos that 1 to 2 weeks have elapsed since the eclosion of the mosquitos and that have not experienced blood sucking are put, the number of mosquitos landing on the arm and the number of mosquitos showing the action of blood sucking behavior in a set period are counted, and a repellent index is determined from the number of mosquitos for each of a test product and a control plot or the number of mosquitos showing the action of blood sucking. Paragraph [0023] of Patent Literature 2 describes that a wire mesh bag in which each of rats treated with a test product and a control product, respectively, is put is fixed in a fabric cage in which mosquitos that 1 to 2 weeks have elapsed since the eclosion of the mosquitos and that have not experienced blood sucking are put, the number of mosquitos landing on each rat and the number of mosquitos showing the action of blood sucking behavior after 3 minutes are counted, and a repellent index is determined from the number of mosquitos for each of the test product and the control plot.

In a testing method described in paragraph [0034] of Patent Literature 3, a resin container of which an opening in the upper portion is covered with a mesh is prepared, and large-sized glass petri dishes are arranged in the vicinities of both ends of the bottom of the container, respectively. A specimen sheet treated with an agent is laid on one petri dish, and an untreated blank sheet is laid on the other petri dish. A small-sized petri dish in which a cotton sheet impregnated with 2 g of 5% sugar water as an attractant bait for a mosquito is put is mounted on the center of each petri dish to make a testing apparatus. One hundred tiger mosquitos (unseparated into male and female) fasting for about 6 hours are sampled into the testing apparatus, and the total number of mosquitos that can be confirmed to land on the large-sized petri dish in each of a specimen area and a blank area within 2 hours is recorded.

In a testing method described in paragraph [0029] of Patent Literature 4, an acrylic resin cylinder having an inner diameter of 10 cm and a length of 100 cm is laterally placed, pieces of gauze are put as filters on portions of 15 cm from both ends of the cylinder, and a movable partition formed of a plastic plate is further disposed on a central portion from both ends of the cylinder. Filter paper having a diameter of 10 cm is impregnated with 0.5 g of each flavoring agent component to be tested, to make sample filter paper. A hole for putting a sample insect is opened in a part of the cylinder wall of one end side, 25 female adult common house mosquitos are released from the hole into the interior of the cylinder, and the hole is closed. Sample filter paper is placed between one end and the gauze filter, the partition in the central portion of the cylinder is then removed, and the number of sample insects moving in a direction from the position of the partition to the other end is chronologically observed.

CITATION LIST

Patent Literature

Patent Literature 1: Unexamined Japanese Patent Application Kokai Publication No. 2005-023439
Patent Literature 2: Unexamined Japanese Patent Application Kokai Publication No. 2006-169209
Patent Literature 3: Unexamined Japanese Patent Application Kokai Publication No. 2010-126486
Patent Literature 4: Unexamined Japanese Patent Application Kokai Publication No. 2013-136524

SUMMARY OF INVENTION

Technical Problem

In the testing apparatus of Patent Literature 1 or 2, when a sample is put in the fabric cage in which mosquitos are put, the mosquitos may escape from the fabric cage. In the testing method of Patent Literature 3, putting of a large number of mosquitoes requires time, and it is impossible to precisely determine a time at which the test is started, because the sample is placed in the resin container in advance, followed by putting the mosquitos therein. Moreover, it is possible only to conduct a competitive test of a specimen and a comparative product.

In the testing apparatus of Patent Literature 4, it is impossible to conduct a test for measuring the effect of the contact of a mosquito with the sample because the sample filter paper of the sample and mosquitos are separated by the gauze. Moreover, an effect that can be tested is limitative because no attractant bait is used. Moreover, the rate of diffusing a specimen material is not taken into consideration.

The present disclosure was made under such circumstances with an objective of more precisely measuring various effects in an insect repellency test while preventing an insect from escaping in the test.

Solution to Problem

An apparatus for testing insect repellency according to a first aspect of the present disclosure includes:

a housing in which an internal space capable of housing an insect is formed, an opening through which the internal space and an outside communicate with each other is formed, and a portion other than the opening is closed so that the insect is incapable of passing through the portion;

a plate-shaped cover that is capable of covering the opening from an external side of the housing;

rails in a pair, which are disposed in parallel with each other on both sides of the opening across the opening on an outer surface of the housing, which maintain a gap between a face, on which the opening is formed, of the housing and the cover to have a size preventing the insect from passing through the gap, and which slidably retain the cover on the external side of the housing; and a sample holder that retains a sample, that is slidably retained by the rails, and that enables the sample to be exposed from the opening to the internal space when being slidably retained by the rails in a state of retaining the sample, wherein the cover and the sample holder retaining the sample can be slid between the rails in the pair in a state in which one side of the cover and one side of the sample holder come into contact with each other, whereby the cover and the sample holder are enable to be moved between a position at which the cover covers the opening and a position at which the sample covers the opening.

A method for testing insect repellency according to an aspect of the present disclosure includes:

a step of putting an insect in the housing of the apparatus for testing insect repellency according to the first aspect, retaining the cover by the rails, and closing the opening with the cover;

a step of retaining a sample in the sample holder;

a sample mounting step of sliding the sample holder between the rails in the pair in a state in which one side of the sample holder in which the sample is retained comes into contact with a side of the cover, to move the sample holder to a position at which the sample covers the opening;

a sample removal step of sliding the cover between the rails in the pair in a state in which the side of the cover comes into contact with the side of the sample holder in which the sample is retained, after a lapse of a set period of time following exposure of the sample from the opening into the internal space, to move the cover to a position at which the sample covers the opening; and a measurement step of measuring the effect of the sample.

Advantageous Effects of Invention

According to the present disclosure, an insect is prevented from escaping in an insect repellency test, and more various effects can be more precisely measured because a sample holder and a cover can be slid between rails in a pair in a state in which one side of the sample holder and one side of the cover come into contact with each other, to move the sample holder and a cover between a position at which the cover covers an opening and a position at which the sample covers the opening.

BRIEF DESCRIPTION OF DRAWINGS

FIG. 17 is a flowchart illustrating an example of a process of an insect repellency test according to Embodiment 2.

DESCRIPTION OF EMBODIMENTS

Figure 1:
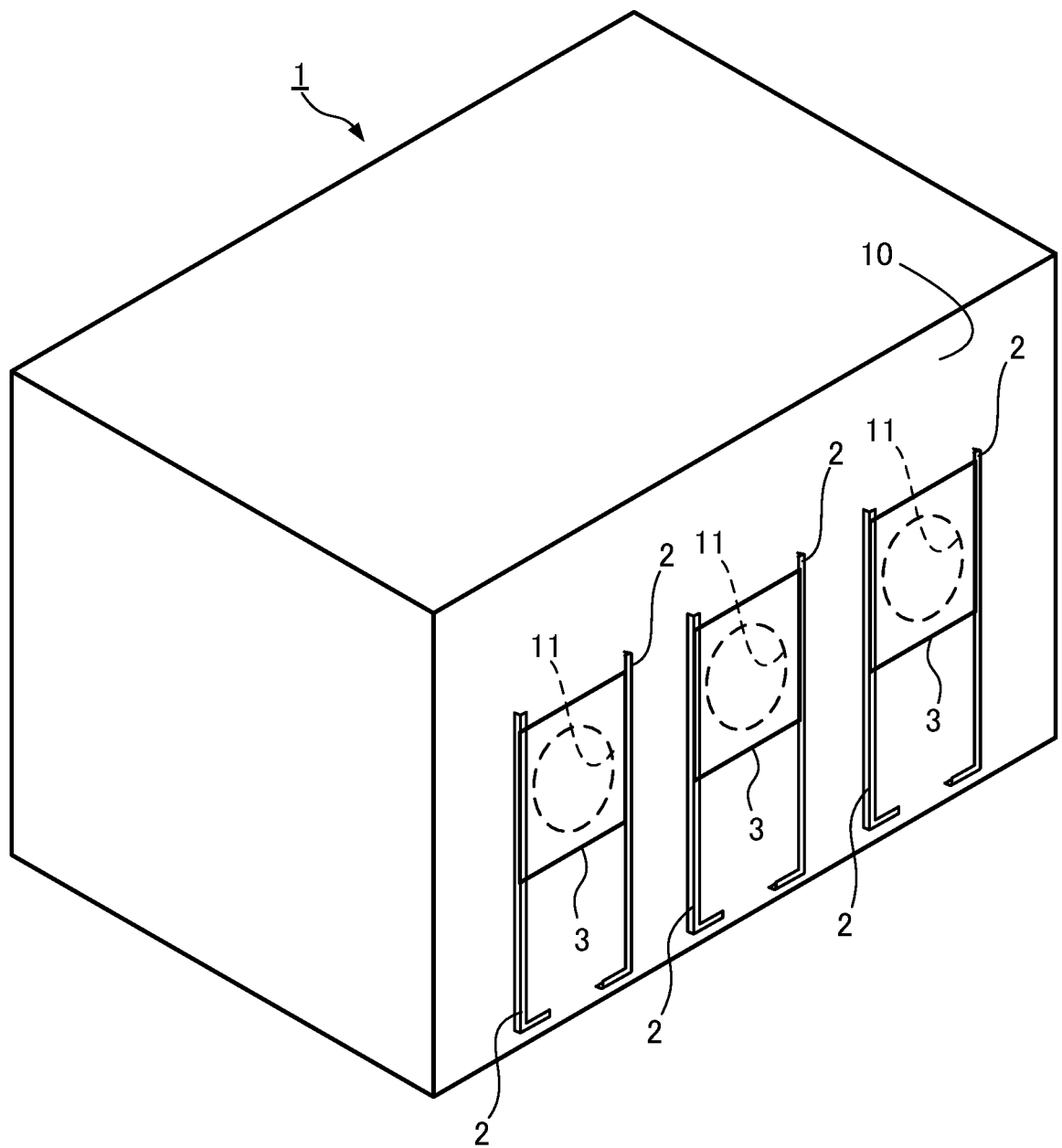
FIG. 1 is a perspective view of an apparatus for testing insect repellency according to Embodiment 1 of the present disclosure.

Embodiments of the present disclosure will be described in detail below with reference to the drawings. In the drawings, the same or equivalent portions are denoted by the same reference signs. In this disclosure, "insect" is the generic name of small animals other than human, beasts, birds, fishes, and shellfishes, and "insect" includes arthropods and annelids.

Embodiment 1

FIG. 1 is a perspective view of an apparatus for testing insect repellency according to Embodiment 1 of the present disclosure. The apparatus for testing insect repellency includes a housing 1 in which openings 11 are formed, a portion other than the openings 11 is closed so that an insect is incapable of passing through the portion, and the insect can be internally housed. The apparatus for testing insect repellency includes plate-shaped covers 3 that can cover the openings 11 from the outside of the housing 1. In the housing 1, rails 2 in a pair, which are parallel to each other, are disposed, for each opening 11, on both sides of each opening 11 across each opening 11 on an outer surface of the housing 1. The rails 2 maintain a gap between the cover 3 and a face, on which the openings 11 of the housing 1 are formed, to have a size preventing the insect from passing through the gap, and slidably retain the cover 3 outside the housing 1.

A face on which the openings 11 of the housing 1 are formed is formed of a plate-like member 10. A part or the whole of the housing 1 is formed of, for example, a transparent resin, and the interior of the housing 1 can be observed. A part or the whole of the housing 1, excluding the face on which the openings 11 are formed, may be formed of a net through which a housed insect is unable to pass.

In the example of FIG. 1, the three openings 11 are formed on the one face of the housing 1. The number of openings 11 may be any number as long as the number is one or more. Openings 11 may be formed on plural faces. The housing 1 is not limited to a rectangular parallelepiped, and may have any shape as long as the shape is a closed three-dimensional shape. The housing 1 may be, for example, a cylinder of which both bottom faces are closed. In such a case, an opening 11 can be formed on a cylindrical face or a bottom face.

A window or hole which is other than the openings 11 and can be opened and closed may be formed in the housing 1. It is preferable to prevent an insect from passing through the window or hole in a period from the closing of the window or hole and putting of the insect into the housing 1 to the end of a test. Even if such a window or hole is formed, the portion other than the openings 11 is closed so that an insect is incapable of passing through the portion, whereby the insect can be housed in the interior of the housing 1.

The housing 1 is not necessarily put so that the face on which the openings 11 are formed is vertical. For example, the housing 1 may be horizontally put so that the face on which the openings 11 are formed is upper or lower. Alternatively, the face on which the openings 11 are formed may be inclined with respect to the horizontal plane.

Figure 2:
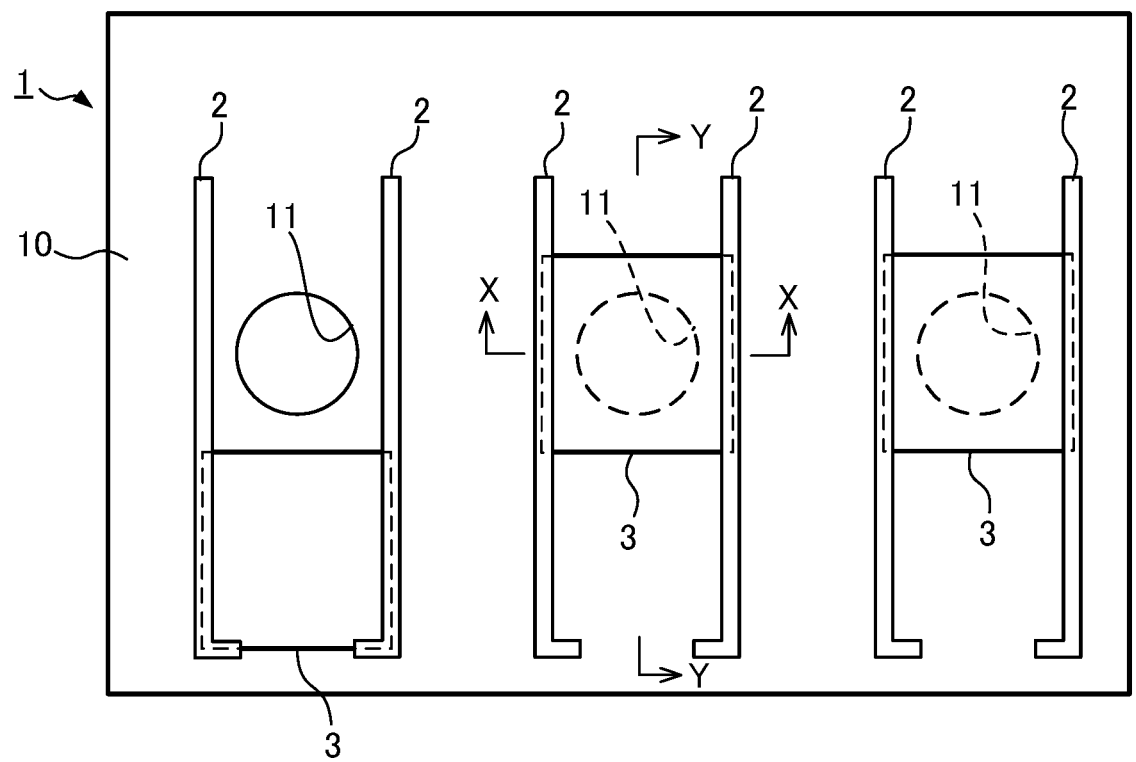
FIG. 2 is a front view of the openings of the apparatus for testing insect repellency according to Embodiment 1.

FIG. 2 is a front view of the openings of the apparatus for testing insect repellency according to Embodiment 1. FIG. 2 illustrates a state in which the cover 3 for closing the most left opening 11 of the three openings 11 is opened, and a state in which the two, more right openings 11 are closed with the covers 3. One ends of the rails 2 are bent in the direction of facing each other so that each cover 3 is prevented from being moved over the ends. Lockers, which are not illustrated, are formed on the cover 3 and the rails 2 or the housing 1 so as to retain the cover 3 at a position at which the cover 3 blocks the opening 11. For example, a spring on which a projection is formed is included on one of the cover 3 and the rails 2, and a notch, into which the projection is fit, is formed on the other.

Figure 3:
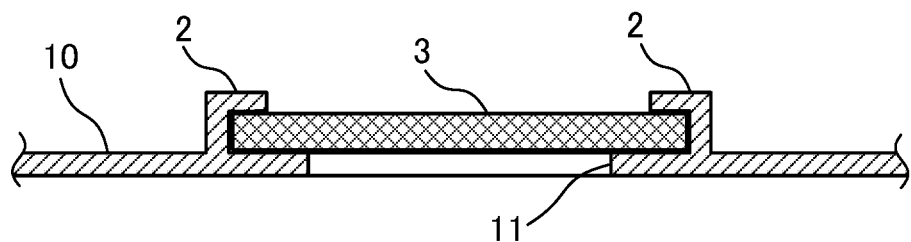
FIG. 3 is a transverse cross-sectional view of an opening of the apparatus for testing insect repellency according to Embodiment 1.

FIG. 3 is a transverse cross-sectional view of an opening of the apparatus for testing insect repellency according to Embodiment 1. FIG. 3 illustrates a cross section taken along the line X-X of FIG. 2. Each of the rails 2 protrudes through the outer surface of the housing 1, and has a shape in which the tips of the rails 2 are bent inwardly in the direction of facing each other, and the cover 3 is sandwiched and retained between the outer surface of the housing 1 and the facing surfaces of the rails 2, facing the outer surface. The cover 3 can slide in the direction orthogonal to the paper face of FIG. 3. The distance between the rails 2 in the pair, facing each other, is greater than the width of the opening 11.

Figure 4:
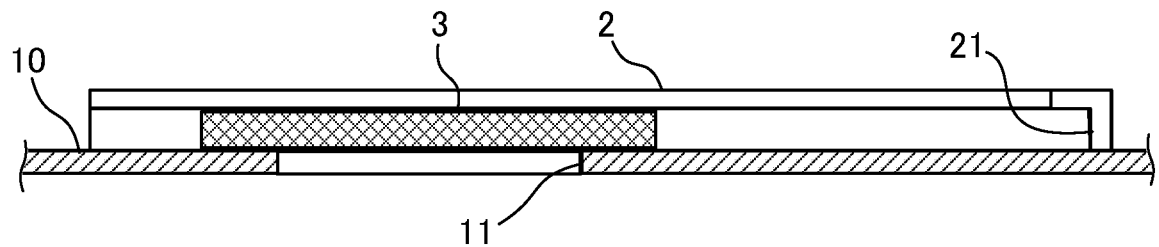
FIG. 4 is a vertical cross-sectional view of an opening of the apparatus for testing insect repellency according to Embodiment 1.

FIG. 4 is a vertical cross-sectional view of an opening of the apparatus for testing insect repellency according to Embodiment 1. FIG. 4 illustrates a cross section taken along the line Y-Y of FIG. 2. The rail 2 is formed to be parallel to the outer surface of the housing 1, faced by the rail 2. One end of the rail 2 is bent inwardly in the facing direction to form a detent 21. It is impossible to move the cover 3 from the opening 11 over the detent 21. An end opposite to the detent 21 of the rail 2 is opened, so that a member having the same cross-sectional shape as the cross-sectional shape of the cover 3 can be inserted between the rail 2 and the housing 1.

Figure 5:
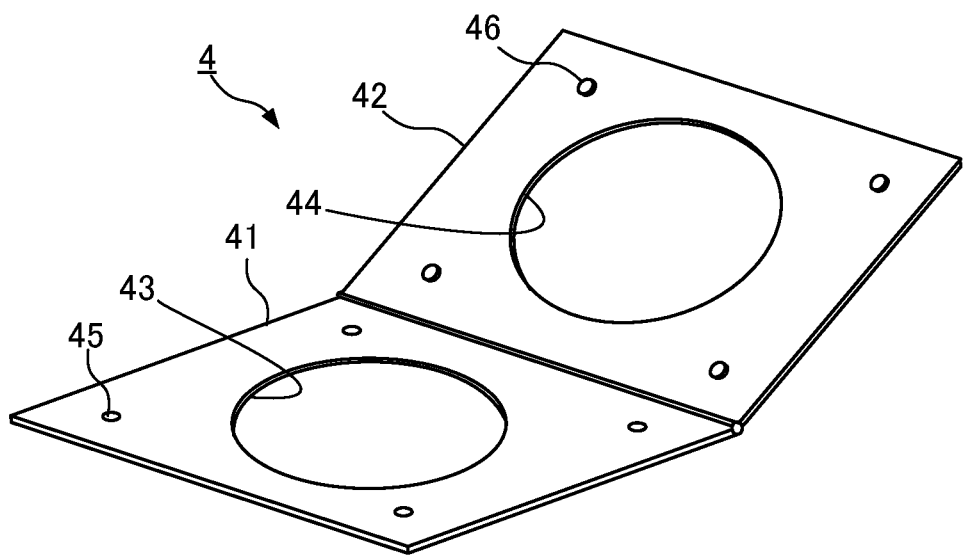
FIG. 5 is a perspective view of a sample holder in the apparatus for testing insect repellency according to Embodiment 1.

FIG. 5 is a perspective view of a sample holder in the apparatus for testing insect repellency according to Embodiment 1. FIG. 5 illustrates a state in which a sample holder 4 is opened. The sample holder 4 includes a plate A 41 and a plate B 42 which are thin and are rotatably coupled to each other through one side of the plate A 41 and one side of the plate B 42. For example, a hinge structure can be used for coupling the plate A 41 and the plate B 42 to each other. Alternatively, the plate A 41 and the plate B 42 may be coupled with a resin that has flexibility and can be repeatedly bent and straightened. Holes 43 and 44 are formed in the plate A 41 and the plate B 42, respectively. The holes 43 and 44 overlap one another to form one through-hole when the plate A 41 and the plate B 42 are closed to overlap one another.

Concave holes 45 are formed in the four corners of the plate A 41, and projections 46 are formed in the four corners of the plate B 42. The projections 46 are fit into the concave holes 45 when the plate A 41 and the plate B 42 are closed to overlap one another. When the plate A 41 and the plate B 42 are closed so that a sheet-like sample is sandwiched between the plate A 41 and the plate B 42, the projections 46 are fit into the concave holes 45, whereby the sample can be fixed so that the sample is prevented from being moved. The sample is, for example, a cloth that is subjected to insect repellent treatment or a cloth that is not subjected to insect repellent treatment. The sample is not limited to a cloth, and may be, for example, a film, paper, or a resin plate that simulates skin, bark, a leaf, or the like. When the plate A 41 and the plate B 42 are closed so that the sheet-like sample is sandwiched between the plate A 41 and the plate B 42, a cross section of the sample holder 4 has the same shape as the shape of a cross section of the cover 3, so that the sample holder 4 retaining the sample can be inserted and slid between the rails 2 and the housing 1.

The plate A 41 and the plate B 42 are not limited to a configuration in which the plate A 41 and the plate B 42 are coupled rotatably to each other. The plate A 41 and the plate B 42 may be separated bodies. The plate A 41 and the plate B 42 are not limited to the structure of the concave holes 45 and the projections 46 if the sample can be fixed so as not to deviate from the holes 43 and 44.

Figure 6:
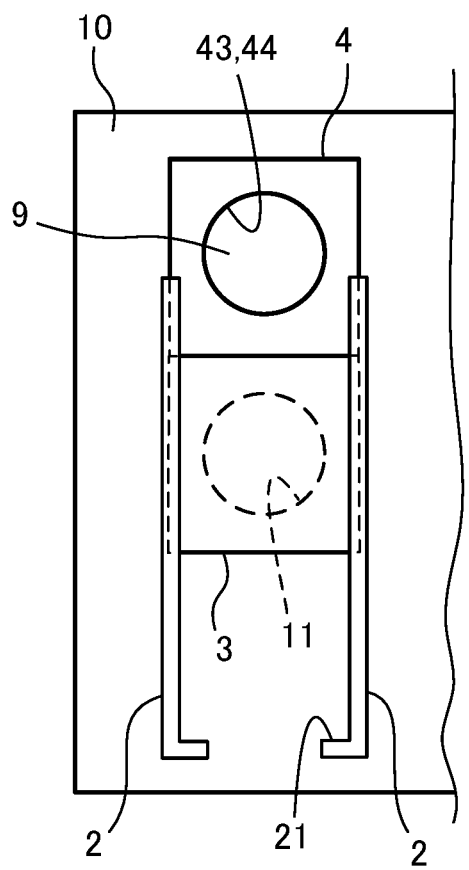
FIG. 6 is a front view illustrating a state in which the sample holder and a cover are allowed to come into contact with each other in the apparatus for testing insect repellency according to Embodiment 1.

FIG. 6 is a front view illustrating a state in which the sample holder and a cover are allowed to come into contact with each other in the apparatus for testing insect repellency according to Embodiment 1. A sample 9 is sandwiched between the plate A 41 and the plate B 42 and retained by the sample holder 4. The sample 9 blocks the holes 43 and 44 of the sample holder 4. FIG. 6 illustrates a state in which the sample holder 4 retaining the sample 9 is inserted between the rails 2 and the housing 1 to allow a side of the cover 3 to come into contact with a side of the sample holder 4 when the cover 3 is at a position at which the opening 11 is closed. The cover 3 and the sample holder 4 can be moved from a position, at which the cover 3 covers the opening 11, to a position, at which the sample 9 retained by the sample holder 4 covers the opening 11, by sliding the cover 3 and the sample holder 4 between the rails 2 in the pair while the side of the cover 3 and the side of the sample holder 4 come into contact with each other. An insect is unable to pass between the cover 3 and the sample holder 4 when the sides, coming into contact with each other, of the cover 3 and the sample holder 4 pass over the opening 11 because the cover 3 and the sample holder 4 are slid while the side of the cover 3 and the side of the sample holder 4 come into contact with each other.

Figure 7:
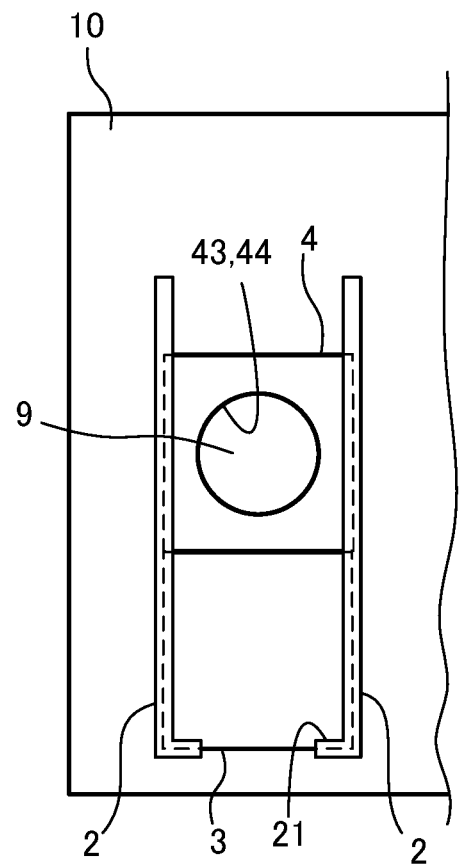
FIG. 7 is a front view illustrating a state in which the sample holder is moved to an opening in the apparatus for testing insect repellency according to Embodiment 1.

FIG. 7 is a front view illustrating a state in which the sample holder is moved to an opening in the apparatus for testing insect repellency according to Embodiment 1. It is possible to move the sample holder 4 to a position, at which the holes 43 and 44 of the sample holder 4 coincide with the opening 11, to expose the sample 9 from the opening 11 into the internal space of the housing 1 because the positions of the opening 11 of the housing 1 and the holes 43 and 44 of the sample holder 4 coincide with each other in the width direction of the rails 2. In such a case, at least a part of the holes 43 and 44 overlap the opening 11 in the direction orthogonal to the face on which the opening 11 is formed.

When the sample holder 4 is moved to the position at which the holes 43 and 44 of the sample holder 4 coincide with the opening 11, the cover 3 just hits the detents 21.

The detents 21 of the rails 2 are not needed when a mechanism for locking the sample holder 4 so that the sample holder 4 can be retained at the position at which the holes 43 and 44 coincide with the opening 11 is formed. The cover 3 may be detached from the housing 1 in a state in which the sample holder 4 is retained at the position of the opening 11. A case in which the cover 3 can be retained at the detents 21 is favorable because the cover 3 has already come into contact with the sample holder 4 and been retained by the rail 2 in removal of the sample holder 4.

Each of FIG. 6 and FIG. 7 illustrates one opening 11. For each of the other openings 11, however, the cover 3 and the sample holder 4 can be slid between the rails 2 in the pair in a similar manner while one side of the cover 3 and one side of the sample holder 4 come into contact with each other, to move the sample holder 4 to the position of the opening 11 and to expose a sample 9 from the opening 11 into the internal space of the housing 1.

In a manner reverse to the state illustrated in FIG. 7, the cover 3 and the sample holder 4 can be reversely slid while the side of the cover 3 and the side of the sample holder 4 come into contact with each other, to move the cover 3 and the sample holder 4 to a position at which the opening 11 is covered with the cover 3. The apparatus for testing insect repellency according to Embodiment 1 enables the position at which the opening 11 is covered with the cover 3 and the position at which the sample 9 is exposed from the opening 11 to be instantly switched while a state in which an insect is prevented from passing is maintained.

When the sample 9 retained by the sample holder 4 is allowed to coincide with the position of the opening 11, the sample 9 is directly exposed from the opening 11 into the internal space of the housing 1, and therefore, it is possible to confirm not only an effect in that the sample 9 attracts an insect or an effect in that the sample 9 repels an insect but also an effect in a case in which an insect comes into contact with the sample 9. Further, when gas or liquid passes through a support for the sample 9, like a cloth, putting of a substance that attracts an insect, for example, an attractant bait on the back surface of the sample support enables an insect to be attracted by the substance put on the back surface of the sample 9 and to be decoyed toward the sample 9. As a result, the effect in that the sample 9 repels an insect or the effect in the case in which an insect comes into contact with the sample 9 can be examined, in a sense, in a further enhancement or amplification manner.

Figure 8:
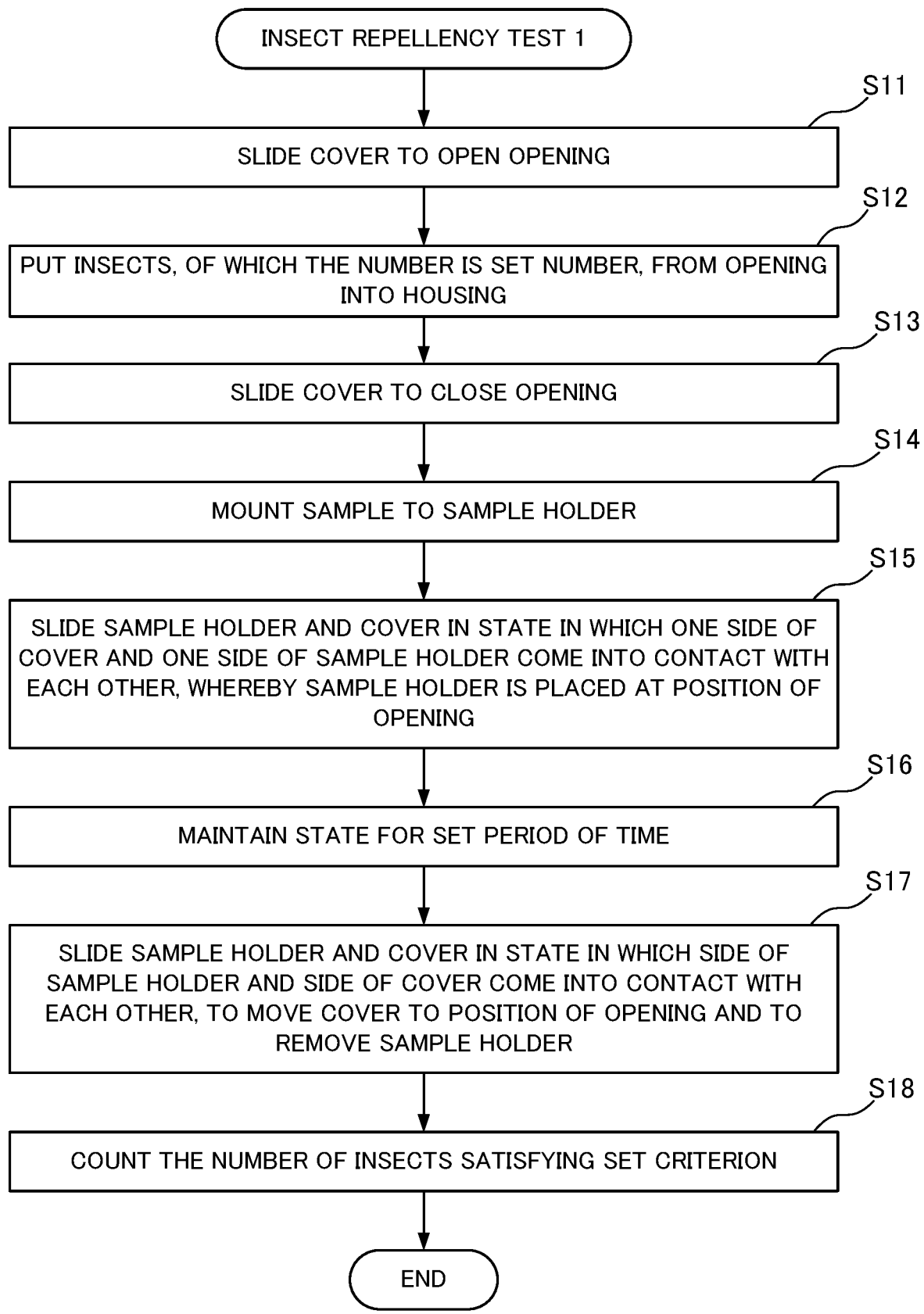
FIG. 8 is a flowchart illustrating an example of a process of an insect repellency test according to Embodiment 1.

FIG. 8 is a flowchart illustrating an example of a process of an insect repellency test according to Embodiment 1. Examples of an insect used in the test include a group of insects bred under a certain condition, for example, mosquitos, fleas, mites, or the like. First, the apparatus for testing insect repellency and the sample 9 are prepared. The cover 3 of the apparatus for testing insect repellency is slid to open the opening 11 of the housing 1 (step S11). Insects of which the numbers of the males and females are set numbers, respectively, are extracted from a group of bred insects and put from the opening 11 into the housing 1 (step S12), followed by immediately sliding the cover 3 to close the opening 11 (step S13). If the housing 1 includes a window or hole that is other than the opening 11 and can be opened and closed, the insects may be put from the window or hole into the housing 1. In this case, the opening 11 is closed with the cover 3.

The sample 9 is mounted to the sample holder 4 (step S14). Depending on the test, an attractant, for example, an attractant bait is mounted on the back surface of the sample 9. In order to mount the attractant, for example, cotton or filter-paper including a liquid of the attractant bait can be affixed to the sample holder 4 closer to the back side of the sample 9 with a pressure sensitive adhesive tape. Then, the cover 3 and the sample holder 4 retaining the sample 9 are slid in a state in which one side of the cover 3 and one side of the sample holder 4 come into contact with each other, whereby the sample 9 retained by the sample holder 4 is placed at the position of the opening 11 (step S15). Such a state is maintained for a set period of time from the placement of the sample 9 at the opening 11 (step S16).

While the sample 9 is exposed from the opening 11 into the internal space of the housing 1, the number of insects landing on the sample 9, the number of insects showing a behavior of sucking the attractant bait, or the number of insects that come into contact with the sample 9 and are influenced by the sample 9 can be observed and measured. Alternatively, the interior of the housing 1 can be photographed, for example, to count the number of insects meeting a set condition or to measure a total period of time for which an insect lands on the sample 9.

After a lapse of a set period of time, the sample holder 4 and the cover 3 are slid in a state in which the side of the sample holder 4 and the side of the cover 3 come into contact with each other, to move the cover 3 to the position of the opening 11 and to remove the sample holder 4 from the housing 1 (step S17). Then, the number of insects satisfying a set criterion is counted (step S18). As described above, the number of insects satisfying the criterion is counted while the sample 9 is exposed from the opening 11 into the internal space of the housing 1, or the opening 11 is covered with cover 3, followed by counting the number of insects fallen on the bottom. The number of the insects satisfying the criterion, a period of time for which the criterion is satisfied, or the like can be regarded as an index representing the effect of the sample 9. If the same test is conducted for a sample 9 to be tested and a sample 9 to be compared, the effect of the sample 9 to be tested with respect to the sample to be compared can be revealed.

As described above, the apparatus for testing insect repellency according to Embodiment 1 prevents an insect from escaping in an insect repellency test and enables a period of time from the start to end of the test to be precisely determined. For the sample 9, it is possible to measure not only an effect in that the sample 9 attracts an insect or an effect in that the sample 9 repels an insect but also an effect in a case in which an insect comes into direct contact with the sample 9. Further, an attractant is arranged on the back surface of the sample 9, and the effect in that the sample 9 repels an insect or the effect in the case in which an insect comes into contact with the sample 9 can be examined, in a sense, in a further enhancement or amplification manner. As a result, more various effects can be more precisely measured.

Figure 9:
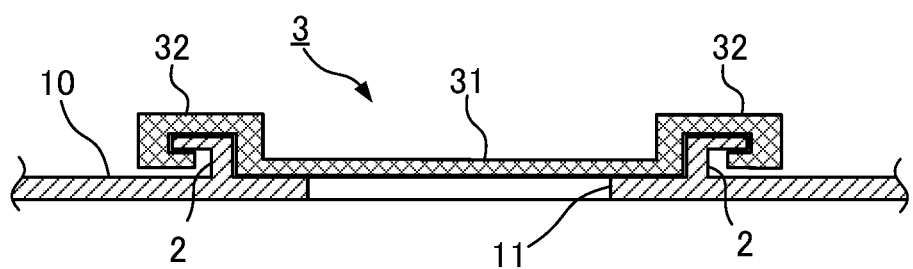
FIG. 9 is a transverse cross-sectional view of rails and a cover according to Alternative Example 1.

FIG. 9 is a transverse cross-sectional view of rails and a cover according to Alternative Example 1. FIG. 9 corresponds to a cross section taken along the line X-X of FIG. 2. In Alternative Example 1, rails 2 are bent outwardly in a direction in which the rails 2 face each other. A cover 3 includes sliders 32 that wrap the rails 2 so as to hold the rails 2, and the ends of the sliders 32 are inwardly bent and are sandwiched between the outer surface of a housing 1 and the facing surfaces of the rails 2. A center 31 of the cover 3 is close to the outer surface of the housing 1 in a state in which the cover 3 is fit into the rails 2. In Alternative Example 1, the rails 2 also maintain a gap between the cover 3 and a face, on which an opening 11 is formed, of the housing 1, so that the gap has such a size that an insect is prevented from passing through the gap, and slidably retain the cover 3 outside the housing 1.

Figure 10:
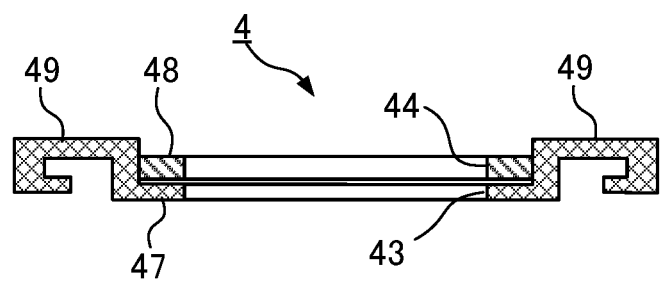
FIG. 10 is a transverse cross-sectional view of a sample holder according to Alternative Example 1.

FIG. 10 is a transverse cross-sectional view of a sample holder according to Alternative Example 1. The sample holder 4 includes a member A 47 and a member B 48. The outer shape of a cross section of the member A 47 is the same as that of the cover 3 of Alternative Example 1, and sliders 49 are formed on both sides of the member A 47. The member B 48 is fit into the recess of the center of the member A 47. Holes 43 and 44 are formed in the centers of the member A 47 and the member B 48, respectively. The holes 43 and 44 overlap one another by fitting the member B 48 into the member A 47. The holes 43 and 44 of the member A 47 and the member B 48 are formed so as to overlap the opening 11 of the housing 1. A sample 9 can be sandwiched and retained between the member A 47 and the member B 48. The sample holder 4 is slidably retained by the rails 2 in the state of retaining the sample 9 and exposes the sample 9 from the opening 11 into the internal space of the housing 1.

In Alternative Example 1, the thickness of the sample holder 4 is not restricted by the rails 2, and therefore, the range of the thickness of the sample 9 that can be used is large. A space above the rails 2 can also be utilized as a space in which an attractant is retained.

Figure 11:
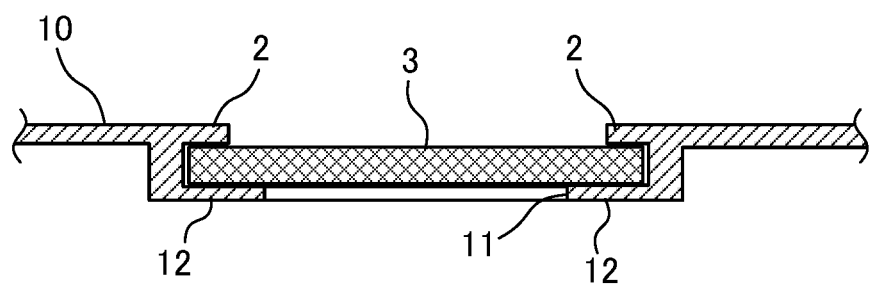
FIG. 11 is a transverse cross-sectional view of rails and a cover according to Alternative Example 2.

FIG. 11 is a transverse cross-sectional view of rails and a cover according to Alternative Example 2. FIG. 11 corresponds to a cross section taken along the line X-X of FIG. 2. In Alternative Example 2, a cover 3 is retained in a side closer to the internal space of a housing 1 than the outer surface of the housing 1. In the housing 1, a bottom 12 with an inwardly concave portion is formed, and rails 2 include protrusions formed by extending the outer surface of the housing 1. The cover 3 is sandwiched and retained between the rails 2 and the bottom 12. An opening 11 in the housing 1 is formed in the bottom 12. The same as the cover 3 and the sample holder 4 in Embodiment 1 can be used as the cover 3 and a sample holder 4 in Alternative Example 2.

The rails 2 of Alternative Example 2 are formed, for example, up to an end face on which the opening 11 of the housing 1 is formed, to enable the cover 3 and the sample holder 4 to be inserted from a side of the housing 1. Alternatively, the rails 2 are formed only up to the middle of an area in which the opening 11 is formed, and the cover 3 and the sample holder 4 can be inserted from a portion without the rails 2. In Alternative Example 2, the sample holder 4 is protruded toward the internal space of the housing 1, and retained, and therefore, the sample 9 can be raised from a plate-like member 10 toward the internal space.

Embodiment 2

Figure 12:
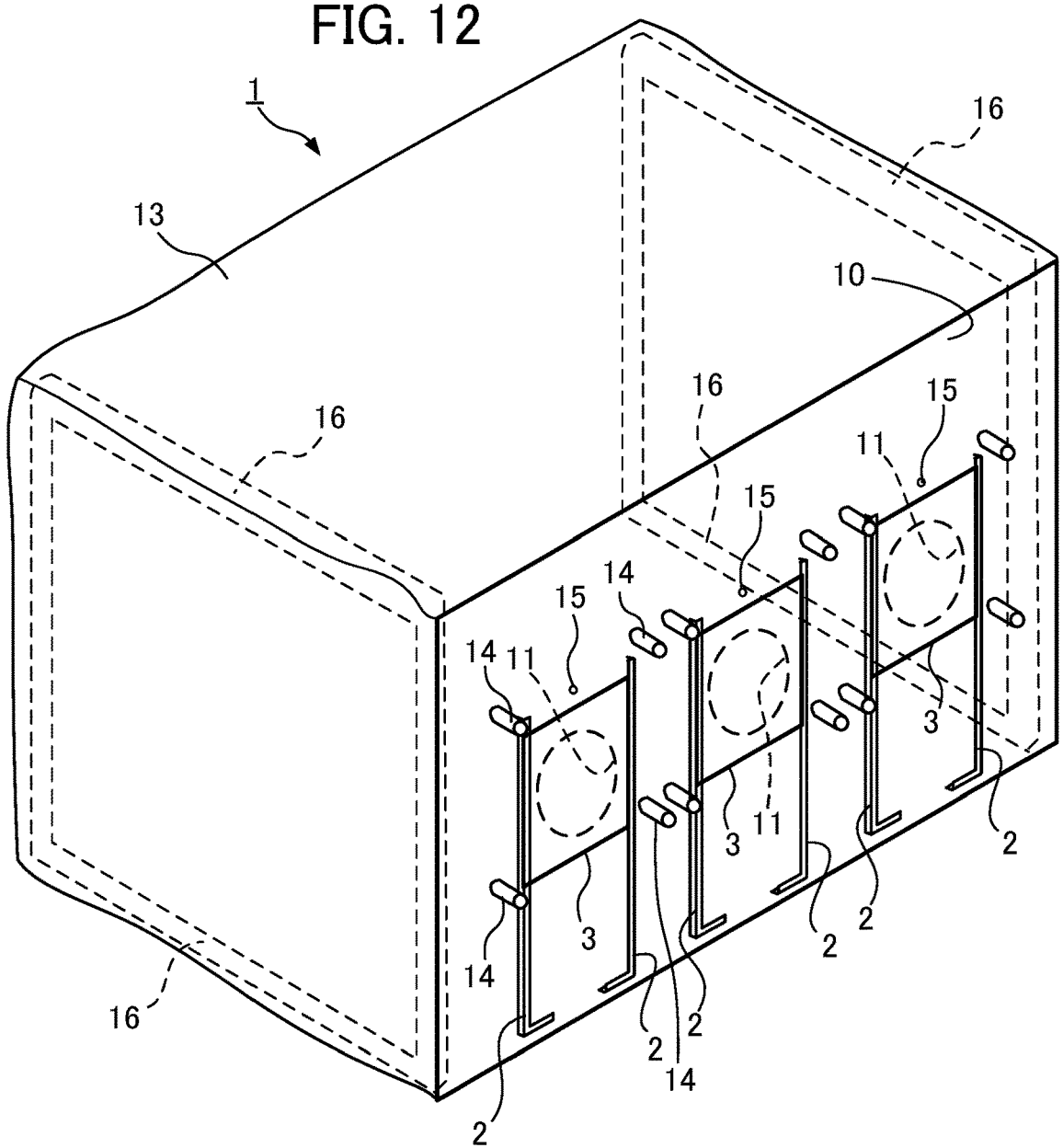
FIG. 12 is a perspective view of a housing portion in an apparatus for testing insect repellency according to Embodiment 2 of the present disclosure.

FIG. 12 is a perspective view of a housing portion in an apparatus for testing insect repellency according to Embodiment 2 of the present disclosure. In Embodiment 2, the portion other than a face on which openings 11 are formed is formed of a net 13 through which an insect is unable to pass, in a housing 1. In addition, the housing 1 includes a mechanism for retaining one side of a feeding apparatus for feeding an insect housed in the internal space of the housing 1, outside the housing 1, in coincidence with the face of the openings 11. Further, inlets 15 through which a substance that attracts an insect or a substance that repels an insect can be injected from the external side of the housing 1 to a side, closer to the internal space, of the face on which the openings 11 are formed are formed in the housing 1. The openings 11, rails 2, covers 3, and sample holders 4 are similar to those of Embodiment 1. In Embodiment 2, the housing 1 is fixed and supported at an angle at which the face on which the openings 11 are formed is inclined with respect to a horizontal plane.

The face on which the openings 11 of the housing 1 are formed is formed of, for example, a resin or metal plate-like member 10. The plate-like member 10 may be transparent. The outer surface, other than the plate-like member 10, of the housing 1 has flexibility and includes a net 13 with a mesh having a size preventing an insect housed in the housing 1 from passing through the mesh. Poles 16 are mounted on the four corners of the plate-like member 10 in order to stretch the net 13 on the plate-like member 10 to form an internal space. The upper portions of the poles 16 on both ends of one side of the plate-like member 10 are linked with a beam to each other in order to reinforce the poles 16. The poles 16 are rotatably supported on the plate-like member 10. By mounting the poles 16 on the plate-like member 10, the net 13 can be stretched to form the internal space in which an insect is housed. The net 13 can be folded by allowing the poles 16 to abut in parallel on the plate-like member 10.

Studs 14 arranged to surround each of the openings 11 are formed on the plate-like member 10 in which the openings 11 of the housing 1 are formed. A feeding apparatus for feeding an insect can be mounted to the studs 14. The inlets 15 penetrating the plate-like member 10 are formed in the plate-like member 10. A substance that attracts an insect or a substance that repels an insect can be injected into the interior of the housing 1 through the inlets 15.

Figure 13:
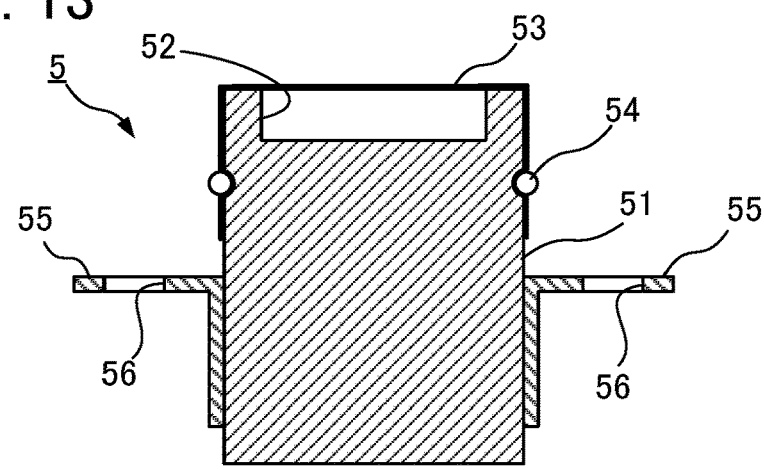
FIG. 13 is a cross-sectional view of a feeding apparatus according to Embodiment 2.

FIG. 13 is a cross-sectional view of a feeding apparatus according to Embodiment 2. The feeding apparatus 5 has an approximately cylindrical shape, and a recess 52 is formed on one bottom surface of a body 51 having a cylindrical shape. The outer diameter of the body 51 has such a size that the body 51 can be fit into holes 43 and 44 in the sample holder 4. A liquid as a bait for an insect is poured in the recess 52, and the liquid is covered with a membrane 53 to retain the liquid. The membrane 53 is fixed with an O-ring 54 fit into a groove formed on a cylindrical outer side. A support plate 55 for mounting the feeding apparatus 5 to the studs 14 is disposed on the cylindrical outer side. Holes 56 into which the studs 14 are fit are formed in the support plate 55. The bottom face on the recess 52 of the feeding apparatus 5 is formed is allowed to coincide with the face of each of the openings 11 of the housing 1 to retain the feeding apparatus 5 outside the housing 1.

The feeding apparatus 5 includes a temperature sensor and a heater which are not illustrated. The temperature sensor and the heater are connected to a control apparatus which keeps the bait liquid at a set temperature and is not illustrated. The liquid which is a bait is selected depending on an insect and a test content. The bait is, for example, the blood of an animal, an aqueous solution of sugar, or sap loved by an insect. In particular, when the blood of an animal is used as the bait for a hematophagous insect such as a mosquito, a flea, or a mite, the temperature of the bait is controlled to be kept approximately at the body temperature of an animal. For example, a plastic paraffin film or an artificial casing for sausage, made from collagen or cellulose, can be used as the membrane 53 for retaining the liquid. The intestine collected from a swine or a sheep, so-called a casing of sausage may be used as the membrane 53. For keeping a feeding condition at a constant level, an artificial film which enables a film thickness to be uniform is preferred to a natural material.

Figure 14:
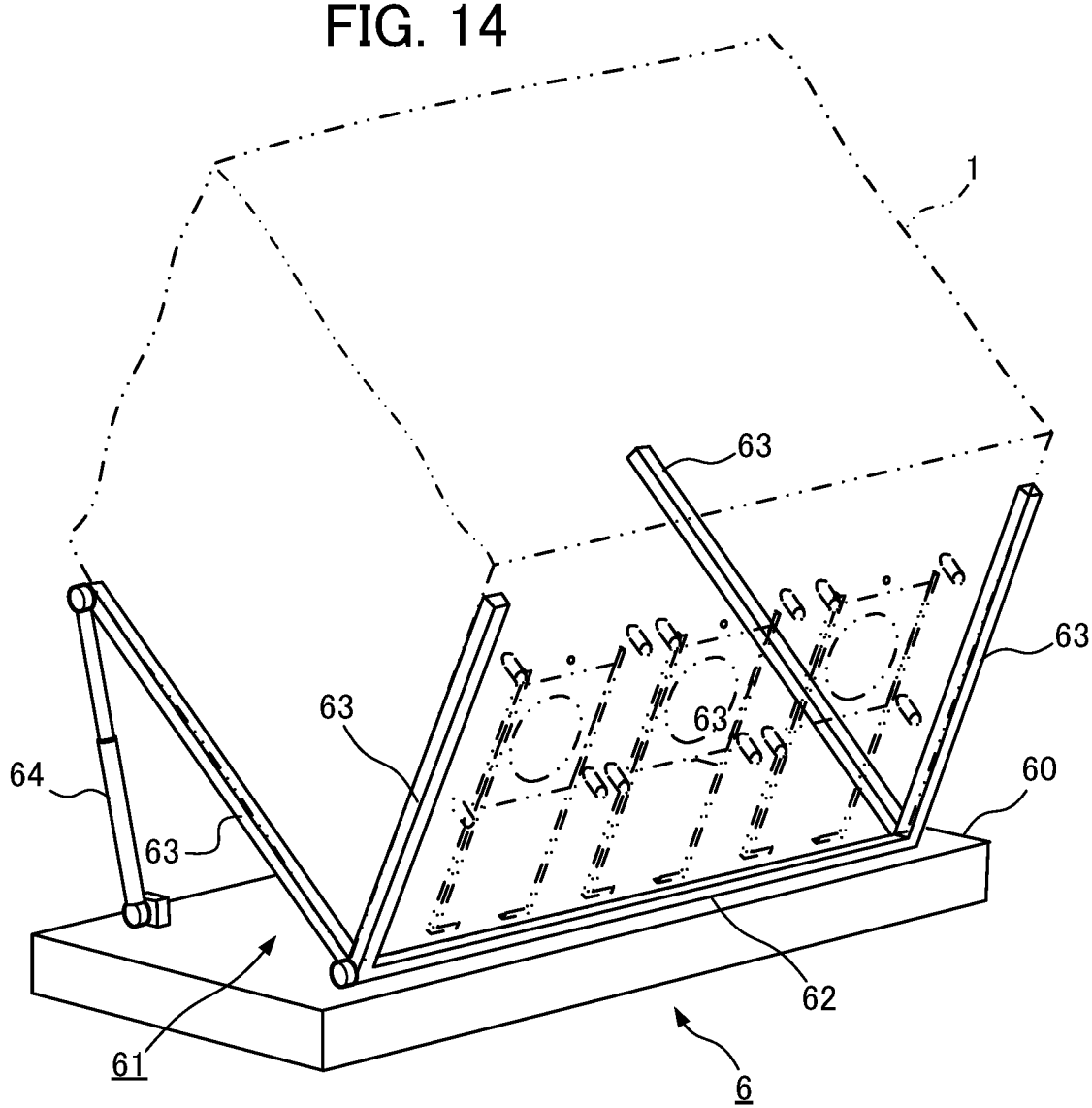
FIG. 14 is a perspective view of a support mechanism for the apparatus for testing insect repellency according to Embodiment 2.

FIG. 14 is a perspective view of a support mechanism for the apparatus for testing insect repellency according to Embodiment 2. A support mechanism 6 includes a base 60, a support frame 61, and struts 64. The support frame 61 includes: a shaft 62 arranged on and in parallel with a surface of the base 60; and arms 63 that extend in two directions orthogonal to the shaft 62 from both ends of the shaft 62. The support frame 61 is supported so as to be able to rotate about the shaft 62 that is parallel to the base 60. One end of each of the arms 63 of the support frame 61 is supported on the base 60 through each of the struts 64 of which the length can be adjusted. One end of each of the struts 64, of which the length can be adjusted, is rotatably supported on the base 60, and the other end is rotatably coupled to each of the arms 63.

In the support mechanism 6, for example, one side of the face on which the openings 11 of the housing 1 are formed is allowed to come into contact with the arms 63 of the support frame 61, and the housing 1 is placed on the support frame 61. The support mechanism 6 is placed on a fixed base which is not illustrated. The support mechanism 6 can rotate with respect to the fixed base and is fixed at a set angle to support the housing 1 on the fixed base. As illustrated in FIG. 14, the housing 1 is fixed and supported at an angle inclined with respect to the horizontal plane so that a side, closer to the internal space, of the face on which the openings 11 are formed is upward.

If a face opposed to the face on which the openings 11 of the housing 1 are formed has strength enabling the housing 1 to be supported, the housing 1 may be placed on the support mechanism 6 while the face on which the openings 11 are formed is allowed to be upward. For example, in the case of the housing 1 of Embodiment 1, the housing 1, of which any side is allowed to abut in parallel on the shaft 62 of the support mechanism 6, may be placed. Alternatively, the base 60 may be formed so that the housing 1 can be fixed to the support mechanism 6 and can be retained below the shaft 62.

The reason why, in the support mechanism 6, an angle is achieved at which the face on which the openings 11 are formed is inclined with respect to the horizontal plane so that the side, closer to the internal space, of the face on which the openings 11 are formed is upward is because the landing of an insect put in the housing 1 on a sample 9 is facilitated. Depending on the kind of an insect to be tested, in a case in which the face of the sample 9 is upward, an insect more easily lands than in a case in which the sample 9 is on the ceiling surface of the housing 1 or a case in which the face of the sample 9 is downward or vertical, and therefore, the effect of the sample 9 can be considered to be more precisely measured.

Depending on the kind of an insect to be tested, the housing 1 is fixed so that the face of the sample 9 is on the ceiling or at an angle inclined downward, or is vertical. The support mechanism 6 enables the angle to be adjusted and fixed so that the face of the sample 9 is optimally oriented, depending on the life of an insect. The angle of the face of the sample 9 is adjusted depending on the life of an insect, whereby a test is conducted under a condition where the number of insects landing on the sample 9 or the number of insects taking a bait is large, and a difference between a test sample and a comparative sample can be more definitely measured.

Figure 15:
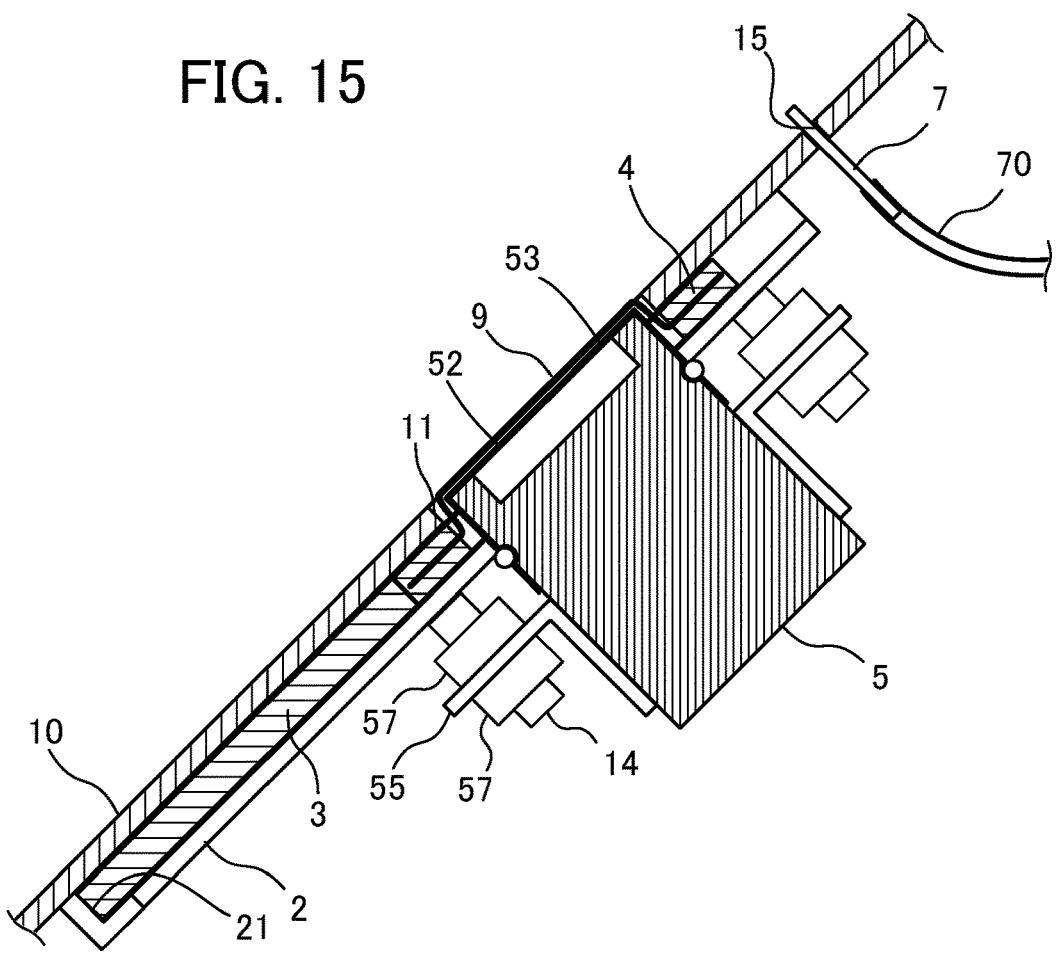
FIG. 15 is a cross-sectional view illustrating the state of setting a sample and the feeding apparatus in the apparatus for testing insect repellency according to Embodiment 2.

FIG. 15 is a cross-sectional view illustrating the state of setting a sample and the feeding apparatus in the apparatus for testing insect repellency according to Embodiment 2. The housing 1 is fixed and supported at the angle at which the face on which the openings 11 of the plate-like member 10 is inclined with respect to the horizontal plane so that the side, closer to the internal space, of the face on which the openings 11 of the plate-like member 10 are formed is upward, and therefore, FIG. 15 illustrates that the face on which the openings 11 are formed is inclined.

The sample 9 is sandwiched and retained by the sample holder 4. The sample holder 4 is retained by the rails 2 at a position at which the sample 9 is exposed from the opening 11 into the internal space. The sample holder 4 is prevented from being downward moved because the cover 3 abuts on the detents 21 of the rail 2, and the sample holder 4 comes into contact with the cover 3. The feeding apparatus 5 is mounted to the studs 14, a bottom face closer to a side, on which a bait is retained, of the feeding apparatus 5 is pressed against the sample 9, and the sample 9 is pushed so as to coincide with the face, closer to the internal space side, of the opening 11. In the feeding apparatus 5, the support plate 55 is fit into the studs 14. The support plate 55 is sandwiched and fixed between, for example, two nuts 57 put on a screw formed on each of the studs 14.

A needle 7 is passed through the inlet 15 formed in the plate-like member 10 to protrude into the internal space. The needle 7 is a hollow tube, of which a leading end includes a formed jet port, and is mounted to a tip of a pipe 70. The pipe 70 is connected to the regulation valve of a syringe or a pressure bottle which is not illustrated. The syringe or the pressure bottle supplies a substance that attracts an insect or a substance that repels an insect.

For example, hematophagous mosquitoes are housed in the housing 1, and the blood of an animal is put as an attractant bait in the feeding apparatus 5. Further, for example, carbon dioxide, as a substance that attracts a mosquito, is injected, with the needle 7, into the side, closer to the internal space, of the face on which the openings 11 are formed. The specific gravity of carbon dioxide is greater than that of air, and therefore, the carbon dioxide moves downward along the plate-like member 10 while being diffused and covers the sample 9 to attract the mosquitoes. The carbon dioxide further flows downward and is discharged through meshes to the outside.

The mosquitos housed in the housing 1 can suck the blood of the feeding apparatus 5 through the sample 9. The number of mosquitos performing a blood sucking behavior in a case in which the sample 9 has the effect of suppressing or inhibiting the blood sucking behavior of a mosquito is expected to be less than the number of mosquitos performing a blood sucking behavior in a case in which the sample 9 has no effect of suppressing or inhibiting the blood sucking behavior of a mosquito. Mosquitos of which the number is predetermined are housed in the housing 1, and the insect repellent effect of the sample 9 can be measured based on the number of mosquitos performing a blood sucking behavior in a set period of time.

A mosquito that has sucked blood stores the sucked blood in the body. Therefore, whether or not a mosquito has sucked blood can be determined by crushing the mosquito and confirming whether the blood is included. Thus, the openings 11 are closed with the covers 3, and the sample 9 is removed, followed by temporarily refrigerating the mosquitos while housing the mosquitos in the housing 1, and by crushing the mosquitoes on a one-by-one basis to count the number of mosquitoes that have sucked blood. Male and female mosquitoes of which the numbers are predetermined, respectively, are housed in advance, and tested, and the number of mosquitoes that have sucked blood or the number of mosquitoes that have not sucked blood among the female mosquitoes can be regarded as an index representing the insect repellent performance of the tested sample 9. The comparison of the number of mosquitoes that have sucked blood or the number of mosquitoes that have not sucked blood in the case of using a support similar to a cloth used for the test, or the like, with the number of mosquitoes that have sucked blood or the number of mosquitoes that have not sucked blood in the case of conducting the same test with a support that is not subjected to insect repellent treatment as a comparative sample enables a difference or ratio between the test sample and the comparative sample to be regarded as the insect repellent performance of the test sample.

In addition to whether or not the bait is taken, an insect repellent effect can be measured based on the number of knocked-down insects in a case in which the sample 9 has the effect of suppressing or disabling the behavior of an insect, for example, in a case in which an insect approaching or coming into contact with the sample 9 is knocked down to become unable to act.

Figure 16:
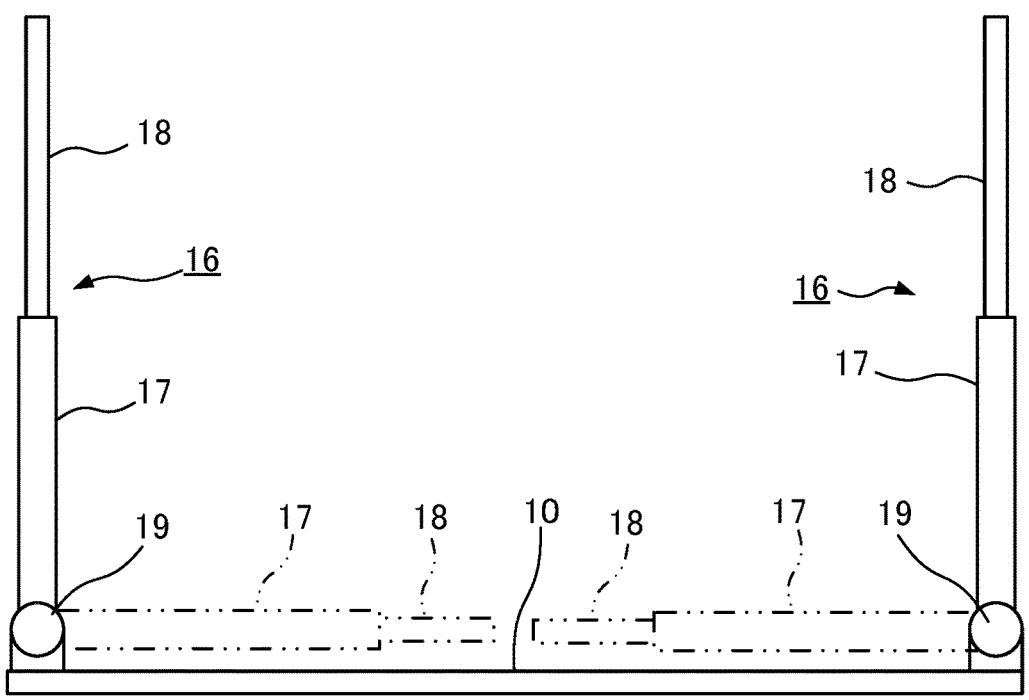
FIG. 16 is a view illustrating the unfolding and folding of a housing in the apparatus for testing insect repellency according to Embodiment 2 of the present disclosure.

FIG. 16 is a view illustrating the unfolding and folding of a housing in the apparatus for testing insect repellency according to Embodiment 2 of the present disclosure. FIG. 16 is a side view of the housing 1 of FIG. 12 in view of the direction of the rails 2. In FIG. 16, the rails 2, the cover 3, the studs 14, and the net 13 are omitted. The poles 16 are supported on the ends of the plate-like member 10 so as to be able to rotate about spindles 19. Each of the poles 16 includes: a pole A 17 having a tubular shape; and a pole B 18 that is slidably housed in the pole A 17. The pole A 17 can keep states in which the pole B 18 is stretched and shortened with respect to the pole A 17. A leading end of the pole B 18 and the pole 16 adjacent to the pole B 18 may be linked with a beam to each other, as illustrated in FIG. 12. The poles 16 are arranged in the interior of the space surrounded by the net 13, as illustrated in FIG. 12.

A state in which the net 13 is stretched is achieved by erecting the poles 16 on the plate-like member 10 in the direction of crossing the plate-like member 10 and stretching the poles B 18. When the poles B 18 are put in the poles A 17 from the state in which the net 13 is stretched, to shorten the poles 16, and the poles 16 are tilted so as to abut in parallel on the plate-like member 10, the net 13 can be allowed to approach the plate-like member 10, and can be folded. The net 13 can be folded even in a state in which an insect is housed in the internal space of the housing 1. The net 13 is a sack, and therefore, the insect is prevented from escaping even if the net 13 is folded.

The net 13 can be folded, and therefore, a space occupying the interior of a refrigerating machine can be downsized when the insect is refrigerated. When the net 13 is folded, the volume of the internal space becomes small, and therefore, the insect can be quickly refrigerated. Moreover, a space in which the housing 1 is stored can be downsized.

The structures of the net 13 and the poles 16 are not limited to the structures illustrated in FIG. 12 and FIG. 16. For example, when the length of a side orthogonal to the plate-like member 10 is less than the half of the length of a side of the plate-like member 10, the lengths of the poles 16 may be fixed. Moreover, the lengths of the poles 16 may be fixed if the poles 16 are permitted to overlap one another when the net 13 is folded. The poles 16 need not be rotated on a plane parallel to a side of the plate-like member 10. For example, the beam that reinforces the poles 16 may be removed so that the poles 16 can be tilted in the directions of the diagonal lines of the plate-like member 10.

The housing 1 is not limited to a structure in which the poles 16 are arranged in the interior of the space surrounded by the net 13. A configuration is acceptable in which the poles 16 are arranged outside the net 13, and the corners of the net 13 are put on the poles 16 as if a mosquito net is hung in the interior of a room. In such a case, it is not necessary to rotatably support the poles 16 on the plate-like member 10 as long as the net 13 can be put on and removed from the poles 16; and a structure is also acceptable in which the poles 16 can be attached to and detached from the plate-like member 10. Further, some poles 16 can be substituted by some arms 63 of the support mechanism 6.

FIG. 17 is a flowchart illustrating an example of a process of an insect repellency test according to Embodiment 2. First, the poles 16 of the housing 1 are erected to unfold the net 13 of the housing 1 (step S20). Step S21 to step S25 are the same as step S11 to step S15 in FIG. 8.

When the cover 3 and the sample holder 4 retaining the sample 9 are slid in a state in which one side of the cover 3 and one side of the sample holder 4 come into contact with each other, whereby the sample 9 retained by the sample holder 4 is placed at the position of the opening 11 (step S25), the housing 1 is placed on the support mechanism 6 (step S26). Step S25 and step S26 may be replaced with each other, and the housing 1 may be placed on the support mechanism 6, followed by placing the sample holder 4 at the position of the opening 11.

Then, the feeding apparatus 5 is mounted (step S27). In such a case, the time of mounting the feeding apparatus 5 is regarded as a time at which the test is started. A substance that attracts an insect is injected from an inlet 15 (step S28), and such a state is maintained for a set period of time (step S29). The substance that attracts an insect may be continuously or intermittently injected. Moreover, a speed at which the substance that attracts an insect is injected is not limited to a constant rate but may be varied.

After a lapse of the set period of time, the feeding apparatus 5 is removed (step S30). In such a case, the time of removing the feeding apparatus 5 is a time at which the test is finished. Then, the housing 1 is removed from the support mechanism 6 (step S31), and the sample holder 4 and the cover 3 are slid in a state in which the side of the sample holder 4 and the side of the cover 3 come into contact with each other, to move the cover 3 to the position of the opening 11 and to remove the sample holder 4 from the housing 1 (step S32). The housing 1 may be removed from the support mechanism 6 after the removal of the sample holder 4.

After the removal of the housing 1 from the support mechanism 6, the net 13 of the housing 1 is folded (step S33). The housing 1 in which the net 13 is folded is put in a freezing chamber, and the insects housed in the housing 1 are refrigerated (step S34). After the temporal refrigeration of the insects, the number of insects satisfying a set criterion is counted (step S35). For example, mosquitoes are crushed, and the number of mosquitoes that have sucked blood is counted.

In a manner similar to the manner of Embodiment 1, the number of insects satisfying the criterion is counted while the sample 9 is exposed from the opening 11 into the internal space of the housing 1, or the opening 11 is covered with cover 3, followed by counting the number of insects fallen on the bottom. While the test is conducted, the insects satisfying the set criterion may be measured from the mounting of the feeding apparatus 5 (step S27) to the removal of the feeding apparatus 5 (step S31), or from the placement of the sample holder 4 on the housing 1 (step S25) to the removal of the sample holder 4 from the housing 1 (step S32). For example, the number of insects approaching a set area from the sample 9, the number of insects landing on the sample 9, a total period of time for which the insects land on the sample 9, the number of knocked-down insects, and/or the like can be measured. The number of insects satisfying a criterion or a total period of time satisfying a criterion can be regarded as an index representing the effect of the sample 9.

For the sample 9 which is subjected to insect repellent treatment and the sample 9 which is not subjected to the insect repellent treatment, the same tests are conducted with insects, which are bred under the same condition, and of which the numbers are the same, respectively. The insect repellent performance of the sample 9 which is subjected to the insect repellent treatment can be evaluated from the respective numbers of insects sucking blood. If the numbers of the insects sucking blood is normalized by the numbers of insects put in the housing 1, the numbers of the insects put in the housing 1 need not be the same.

On the assumption that the number of the insects put in the housing 1 in the case of the sample 9 which is subjected to the insect repellent treatment is Nt, the number of the insects sucking blood in the case of the sample 9 which is subjected to the insect repellent treatment is nt, the number of the insects put in the housing 1 in the case of the sample 9 which is not subjected to the insect repellent treatment is Nc, and the number of the insects sucking blood in the case of the sample 9 which is not subjected to the insect repellent treatment is nc, for example, the effect of insect repellent treatment can be evaluated based on the following equations.

Difference between rates of the numbers of insects sucking blood $nc/Nc - nt/Nt$ (1)

Ratio between rates of the numbers of insects sucking blood $(nc/Nc)/(nt/Nt)$, wherein $nt \neq 0$ (2)

Ratio between rates of the numbers of insects which do not suck blood $(1-(nt/Nt))/(1-(nc/Nc))$, wherein $nc \neq Nc$ (3)

In the case of Nt=Nc, normalization is not necessary, and the evaluation can also be performed based on, for example, the following equation.

Difference between the number of insects sucking blood $nc-nt$ (4)

The higher value of the above-described equation represents a higher insect repellent effect. In contrast, in order to allow the lower value to represent a higher insect repellent effect, the sign of the difference is inverted, or the ratio is made to be an inverse.

Instead of the number of insects sucking blood, the number of knocked-down insects, the number of insects dying, the number of insects landing on the sample 9, or a total period of time for which insects land on the sample 9 can be used to evaluate the insect repellent effect.

The above-described embodiments can be used in combination. For example, the support mechanism 6 of FIG. 14 can be used as a structure for supporting the housing 1 of Embodiment 1. For example, when a housed insect is as small as a mite and is able to pass through the net 13, the outer surface of the housing 1 is required to be composed of a resin or metal plate. In such a case, the side, closer to the internal space, of the face on which the openings 11 are formed is preferably made to be upward so that a mite easily approaches the sample 9. The support mechanism 6 of Embodiment 2 enables the angle of the face on which the openings 11 are formed to be changed and therefore enables the face, on which the sample 9 is mounted, to be set at an optimal angle in accordance with the characteristics of the housed insect.

In addition, the apparatus for testing insect repellency of Embodiment 2 can also be modified. For example, the support mechanism 6 is not limited to the example of FIG. 14. If it is not necessary to change the angle of the face on which the openings are formed, it is not necessary to rotatably support the support frame 61, and the support frame 61 can be fixed to the base 60. In such a case, the structure of the shaft 62 and the arm 63 is not needed, and a table having a predetermined shape can be used.

Further, the support mechanism 6 may be mounted on the housing 1. Even when the housing 1 is rotatably supported, the support mechanism 6 can be fixed to the housing 1. In such a case, the support mechanism 6 can be configured so as to be able to be folded to approach the plate-like member 10 of the housing 1.

For example, a portion on which the feeding apparatus 5 is mounted is not limited to the housing 1. For example, a configuration in which the feeding apparatus 5 is mounted on the support mechanism 6 is also acceptable. A crosspiece is constructed between the arms 63 of the support mechanism 6, and the feeding apparatus 5 can be mounted on the crosspiece. The feeding apparatus 5 may be mounted on the sample holder 4. Alternatively, the sample holder 4 and the feeding apparatus 5 may be integrally formed. In such a case, the feeding apparatus 5 is supported by the rails 2. In such a case, the rails 2 and the sample holder 4 may be allowed to have such structures as illustrated in FIG. 9 and FIG. 10. When the feeding apparatus 5 is mounted on the sample holder 4, or when the sample holder 4 and the feeding apparatus 5 are integrally formed, the sample 9 and the feeding apparatus 5 can be simultaneously placed in the housing 1.

The structure in which the feeding apparatus 5 is mounted is not limited to the studs 14 and the nuts 57. For example, a configuration is acceptable in which a cam is formed, and a rotatably supported lever is included. In such a case, each stud 14 can be sandwiched and fixed by the cam by rotating the lever. In addition, a structure is also acceptable in which a frame formed to sandwich the feeding apparatus 5 is disposed, the rails 2 are formed on one of the frame and the feeding apparatus 5, and a groove into which the rails 2 are fit is formed on the other. It is also acceptable to slidably fit the groove into the rails and to mount the feeding apparatus 5.

The apparatus for testing insect repellency of Embodiment 2 can be used in various tests as well as the testing method described above. It will be appreciated that the same test in the apparatus for testing insect repellency of Embodiment 2 as that in the apparatus for testing insect repellency of Embodiment 1 can be conducted. In addition, for example, only the effect of a substance injected from the inlets 15 can be tested. A test can be conducted in which the sample 9 retained by the sample holder 4 and the feeding apparatus 5 are allowed to be the same, and the substance injected from the inlets 15 is changed. In such a case, the number of insects landing on the sample 9, the number of insects taking a bait, or a total period of time for which insects land on the sample 9 is measured, and the effect of attracting an insect by the injected substance or the effect of repelling an insect by the injected substance can be evaluated. The injected substance may be not only a gas but also a sprayed liquid or a scattered powder.

In addition, it is also possible to test the effect of a repellent applied to the skin. For example, the sample is directly applied to a surface of the feeding apparatus 5 without the use of a support for the sample and is placed in the opening 11 of the housing 1. To that end, a structure in which the feeding apparatus 5 is mounted on the sample holder 4, or a structure in which the sample holder 4 and the feeding apparatus 5 are integral is used. In the case of this test, the sample retained by the sample holder 4 is an agent applied to the feeding apparatus 5. For example, the test can be conducted in the cases of applying an agent including a component repelling an insect and an agent that does not include the component to the surface of the feeding apparatus 5. In such a case, the effect of the component repelling an insect can be evaluated by measuring the number of insects landing on the feeding apparatus 5, the number of insects taking a bait, or a total period of time for which insects land on the feeding apparatus 5.

Further, the apparatus for testing insect repellency of each of the embodiments can be combined with a measurement apparatus. For example, light-emitting and light-receiving elements for laser light are arrayed, in the interior of the housing 1, to face each other at a certain distance from the sample 9, and the number of insects approaching or coming into contact with the sample 9 can be measured by counting the number of insects crossing laser light. Moreover, a photograph device and a picture recorder can be used for measuring the number of insects landing on the sample 9 or a total period of time for which insects land on the sample 9. Further, the number of insects satisfying a set criterion can be counted using an image recognition apparatus on the basis of a photographed image.

In a case in which the interior of the housing 1 is photographed, the photograph device may be placed in the interior of the housing 1 because precise determination is precluded by photographing from the outside through the net 13 of Embodiment 2. For example, the photograph device can be mounted on one of the poles 16 to photograph an area including the sample 9.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

REFERENCE SIGNS LIST

1 Housing
2 Rail
3 Cover
4 Sample holder
5 Feeding apparatus
6 Support mechanism
7 Needle
9 Sample
10 Plate-like member
11 Opening
12 Bottom
13 Net
14 Stud
15 Inlet
16 Pole
17 Pole A
18 Pole B
19 Spindle
21 Detent
31 Center
32 Slider
41 Plate A
42 Plate B
43 Hole
44 Hole
45 Concave hole
46 Projection
47 Member A
48 Member B
49 Slider
51 Body
52 Recess
53 Membrane
54 O-ring
55 Support plate
56 Hole
57 Nut
60 Base
61 Support frame
62 Shaft
63 Arm
64 Strut
70 Pipe

The invention claimed is:

1. An apparatus for testing insect repellency, the apparatus comprising:
   a housing in which an internal space capable of housing an insect is formed, an opening through which the internal space and an outside communicate with each other is formed, and a portion other than the opening is closed so that the insect is incapable of passing through the portion;
   a plate-shaped cover that is capable of covering the opening from an external side of the housing;
   rails in a pair, which are disposed in parallel with each other on both sides of the opening across the opening on an outer surface of the housing, which maintain a gap between a face, on which the opening is formed, of the housing and the cover to have a size preventing the insect from passing through the gap, and which slidably retain the cover on the external side of the housing; and
   a sample holder that retains a sample, that is slidably retained by the rails, and that enables the sample to be exposed from the opening to the internal space when being slidably retained by the rails in a state of retaining the sample,
   wherein the cover and the sample holder retaining the sample are slid between the rails in the pair in a state in which one side of the cover and one side of the sample holder come into contact with each other, whereby the cover and the sample holder are enabled to be moved between a position at which the cover covers the opening and a position at which the sample covers the opening.

2. The apparatus according to claim 1, wherein
   in the housing, the two or more openings are formed, and the rails in the pair are formed in correspondence with each of the openings, and the apparatus comprises the cover and the sample holder in correspondence with each of the openings.

3. The apparatus according to claim 1, wherein the housing is fixed and supported at an angle at which a face, closer to the internal space, of a face on which the opening is formed is inclined with respect to a horizontal plane.

4. The apparatus according to claim 1, comprising a support mechanism that is able to be rotated with respect a fixed base and that is fixed at a set angle to support the housing on the fixed base.

5. The apparatus according to claim 1, wherein an inlet through which a substance that attracts the insect or a substance that repels the insect is able to be injected from an external side of the housing to a side, closer to the internal space, of a face on which the opening is formed is formed in the housing.

6. The apparatus according to claim 1, wherein the housing comprises:
a plate-like member forming a face on which the opening is formed;
a pole-like member supported by the plate-like member; and
a net of which a periphery is fixed to the plate-like member, which is stretched by the pole-like member to form a space in which the insect is able to be housed when the pole-like member is erected in a direction of crossing the plate-like member, and which has flexibility, and the net is able to be folded to abut in parallel on the plate-like member.

7. The apparatus according to claim 1, wherein the sample holder comprises two frames between which the sample is able to be sandwiched and retained, and a hole of which at least a part overlaps the opening is formed in a direction orthogonal to a face on which the opening is formed when each of the two frames is retained by the rails at a position at which the opening is covered in a state in which the sample is retained.

8. The apparatus according to claim 7, comprising a mechanism that retains a feeding apparatus on an external side of the housing so that one face of the feeding apparatus that feeds the insect housed in the internal space coincides with the face of the opening.

9. A method for testing insect repellency, the method comprising:
a step of putting an insect in the housing of the apparatus according to claim 1, retaining the cover by the rails, and closing the opening with the cover;
a step of retaining a sample in the sample holder;
a sample mounting step of sliding the sample holder between the rails in the pair in a state in which one side of the sample holder in which the sample is retained comes into contact with a side of the cover, to move the sample holder to a position at which the sample covers the opening;
a sample removal step of sliding the cover between the rails in the pair in a state in which the side of the cover comes into contact with the side of the sample holder in which the sample is retained, after a lapse of a set period of time following exposure of the sample from the opening into the internal space, to move the cover to a position at which the sample covers the opening; and
a measurement step of measuring the effect of the sample.

* * * * *